United States Patent [19]
Kobsa et al.

[11] Patent Number: 5,299,133
[45] Date of Patent: Mar. 29, 1994

[54] METHOD FOR DETERMINING AND CONTROLLING FIBER LUSTER PROPERTIES

[75] Inventors: Henry Kobsa, Greenville, Del.; Barry Rubin, Glen Mills, Pa.; Stephen M. Shearer; David L. Filkin, both of Wilmington, Del.

[73] Assignee: E. I. Du Pont de Nemours and Company, Wilmington, Del.

[21] Appl. No.: 526,853

[22] Filed: May 22, 1990

[51] Int. Cl.$^5$ .................. G06F 15/46; G06F 15/70
[52] U.S. Cl. .................... 364/468; 364/470; 364/578
[58] Field of Search ............... 364/468, 470, 578, 526

[56] References Cited

U.S. PATENT DOCUMENTS

| | | | |
|---|---|---|---|
| 4,954,976 | 9/1990 | Noonan | 364/526 X |
| 4,984,181 | 1/1991 | Kliman et al. | 364/578 X |
| 5,016,183 | 5/1991 | Shyong | 364/470 |

FOREIGN PATENT DOCUMENTS 0199552 10/1986 European Pat. Off.
2190190 11/1987 United Kingdom.

OTHER PUBLICATIONS

L. Vanderheydt et al., "Two-Dimensional Shape Decomposition Using Fuzzy Subset Theory Applied to Automated Chromosome Analysis", Pattern Recognition, vol. 13, No. 2, 1981, pp. 147-157.

K. Bouatouch et al., "LGRC: a language for image synthesis by ray casting", Technology and Science of Informatics, vol. 6, No. 3, Jun. 1987, pp. 221-235.

N. Kiryati et al., "Calculating Geometric Properties From Fourier Representation", Pattern Recognition, vol. 22, No. 5, 1989, pp. 469-475.

*Primary Examiner*—Jerry Smith
*Assistant Examiner*—Paul Gordon
*Attorney, Agent, or Firm*—Rothwell, Figg, Ernst & Kurz

[57] ABSTRACT

A method of determining luster characteristics of fiber filaments utilizing a mathematical model of filament cross sectional shape and simulated impinging light to determine light distribution after interaction with the fiber and thereby determine luster properties. The method also includes a method for deriving individual filament cross sectional shapes of fibers in a bundle of touching filaments and for deriving therefrom other fiber properties and controlling the manufacturing parameters affecting such properties as well as luster properties.

25 Claims, 4 Drawing Sheets

Microfiche Appendix Included
(5 Microfiche, 284 Pages)

METHOD FOR DETERMINING AND CONTROLLING FIBER LUSTER PROPERTIES

MICROFICHE APPENDIX

Attached hereto are five microfiche containing 284 frames of programs and flowcharts which can be employed in the disclosed embodiments and in other embodiments of the present invention. These microfiche are hereby incorporated herein by reference.

This invention relates to a method for determining and controlling fiber luster properties and for determining and controlling certain physical parameters which govern such properties. The invention has particular application to the design and manufacture of fiber and fiber yarns used for textile yarn applications and more particularly for use as carpet yarns. The invention is further applicable to the design and control of certain physical properties of the fibers on which luster depends and for effecting the manufacturing process control of such physical properties irrespective of their relationship to luster.

BACKGROUND

The lustrous appearance of fiber yarns, such as those used in textile and carpet applications, can be characterized in terms of various optical parameters such as those related to reflection and refraction of impinging visible light arising a air-polymer and polymer-air interfaces of individual filaments comprising the yarn. These effects lead to subjective responses in observers of a finished carpet which, for example, may be expressed as brightness and contrast. Brightness and contrast are used herein as components of the luster appearance of a carpet along with bulk of the carpet yarn. Yarn luster is a complex fuction of the cross sectional shape of the filaments comprising the yarn.

Direct measurement of yarn luster is difficult to accomplish or to express in a mathematical sense. A discussion of yarn luster properties and its dependence on filament cross section may be found in U.S. Pat. No. 3,367,100 - Hughey, issued Feb. 6, 1968. Cross sectional shape of the filaments in a given yarn is, in turn, dependent upon the characteristics of the orifices in the spinneret plates used to produce the yarn. The actual shape imparted to a filament by the spinneret orifice is difficult to predict as is well known in the art and explained, for example, in U.S. Pat. No. 3,478,389 - Bradley et al., issued Nov. 18, 1967.

Fiber cross sectional geometries other than circular are widely employed to achieve both desired higher and lower levels of lustrous appearance of fibers for such applications. Other special geometries, such as symmetric and asymmetric multilobal cross sections, are used to impart desirable and esthetically pleasing appearance properties associated with the degree of fiber luster.

At the present time, the available processes for determining and rating such properties are largely subjective and the search for new fiber cross sections and the examination of their influence on the yarn produced from such fibers is therefore time consuming and expensive. Furthermore, because of such limitations, it has not been possible to control such properties as a part of manufacturing operations.

In addition, presently known techniques for determining analytically the actual cross sectional shape of fibers in yarns and for deriving and expressing such shapes in a mathematical format are subject to certain limitations. The conventional fiber cross sectional shape descriptors for non-round fibers are modification ratio ("MR"), the ratio of the diameters D of the circumscribed to inscribed circles, tip ratio ("TR"), the ratio of the diameters of the circle inscribed within an arm to the circumscribed circle, and arm angle ("AA"), the angle defined by tangents to the arm at the points of inflection. Such techniques are described in detail, for example, in U.S. Pat. Nos. 2,939,201 - Holland and 4,492,731 - Bankar et al. The use of the parameters MR, TR and AA serve well in many cases but are subject to certain limitations. In particular, they have limited value for even slightly asymmetrical versions of multilobal fiber products.

SUMMARY OF THE INVENTION

The present invention provides a method for rapidly determining and controlling in a completely objective manner and without subjective intervention the properties of fibers for yarns and other applications on which lustrous appearance depends. The invention provides, in one embodiment thereof, a method for simulating the interaction of light with selected models of individual fibers over a selected range of directions of the impinging light for particular fiber orientations and determining the reflection and refraction behavior of the impinging light in relation to a selectively positioned theoretical observer based on the cross sectional geometry of the fiber utilized as the selected model, and based thereon determining the properties which are determinative of lustrous appearance.

The method of the invention provides for utilizing a mathematically represented selected cross sectional shape for a particular fiber model and calculating based thereon ray trace optics for a series of photons which are assumed to strike the fiber model at random over a range of discrete selected source directions. The photons of incident light which an observer would see are collected discretely and counted in each of the windows of selected directionality. The fiber cross sectional model is indexed over a range of selected discrete orientations and the process just described is repeated for each selected fiber orientation. The process is repeated until a full range, preferably 360 degrees, of sequentially indexed fiber rotation is completed and the photon ray paths are traced over the directional range at each orientation of the fiber.

The data collected from the complete scan as described above are then utilized to calculate the lustrous properties of the fiber. The mathematical model of the cross sectional shape of the selected fiber may be mathematically depicted, for example, in the format of x,y,z orthogonal coordinate axes with the z axis preferably running perpendicular to the plane of the cross section and near the approximate center thereof. In one embodiment of the present invention, however, it is preferred that the cross sectional shape of the fiber be represented mathematically by utilizing a Fourier series description of the fiber cross sectional shape contour. This approach is described later in detail and is referred to as the "Fourier shape descriptor method".

Another aspect of the present invention relates to an improved method for deriving and expressing a mathematical representation of the cross sectional shapes of a physical grouping of individual fibers in a touching configuration, such as in a yarn formed as a composite of individual fibers, and for utilizing the mathematical expressions so derived to determine the lustrous properties of the fibers and the yarn using the mathematical model scanning technique described in summary form above. This aspect of the invention is applicable, for example, to the manufacturing process control and quality control of the fiber manufacturing process to yield fibers having more precisely controlled lustrous properties.

The invention will be better understood and other features, advantages and applications thereof will become apparent from the detailed description which follows taken in combination with the accompanying drawings.

DETAILED DESCRIPTION OF THE INVENTION

Figure 1:
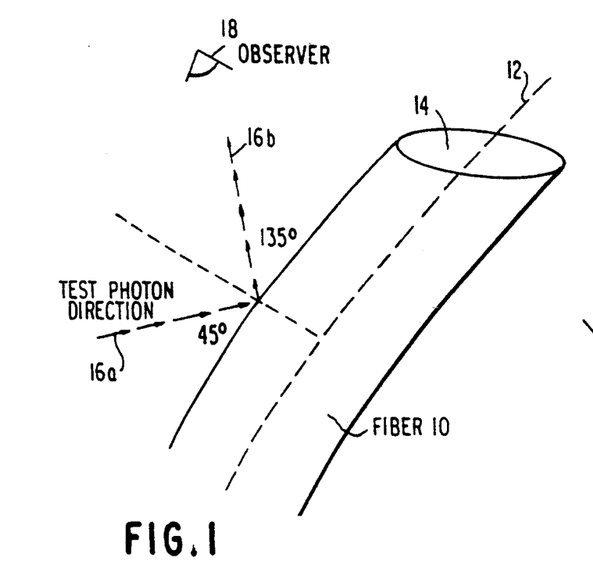
FIG. 1 is a perspective view of a portion of a single fiber showing the approximate axis thereof and illustrating the path of a random photon impinging on and interacting with the fiber and being reflected therefrom toward an observer.

Referring to FIG. 1, there is shown a portion of a fiber 10 having a longitudinal axis 12 and a cross sectional shape shown generally at 14. A photon of light is shown interacting with the fiber 10 along a path 16 comprising an impinging path 16a and a reflected path 16b illustrated along the line of sight of an eye 18 of an arbitrarily positioned observer. In the illustration of FIG. 1, the angles of incidence and reflection as measured from the fiber axis are shown as 45 degrees and 135 degree respectively.

The method of the present invention simulates the interaction of light with an individual fiber, such as that illustrated in FIG. 1, by allowing a large number of light photons to interact randomly with an individual fiber of a selected cross sectional shape over a selected range of angles of incidence of the impinging photons. These simulated test photons are reflected, refracted or miss the fiber entirely.

In the method of the present invention, the directionality of the photons emerging from the fibers toward an observer has been determined to be an important parameter to be considered. Photons emitted from the plane of a carpet and arriving "from under the feet of an observer" comprise a greater fraction of the photons received by the observer when compared with the number of photons originating from an overhead light source and reaching the observer from low angles of reflection, such as those received by an observer of a carpet in a long hallway. For the purpose of luster analysis as presented in a preferred form of the present invention, fibers are assumed to be oriented at an angle of 45 degrees from the horizontal plane of the carpet in relation to the observer.

In each case, the fate of each of the single simulated test photons is accounted for, including the effects of the photon polarization being parallel or perpendicular to the fiber axis 12. In the embodiment to be described, the model used does not consider scattering of light within the fiber and all photons emerge as a cone of light at the specular angle. The information contained in the angular distribution of light intensity around the cone of specular reflection is utilized to determine the luster of the fiber. In this model, any photons of light passing through the fiber emerge on the other side thereof and are assumed lost to the observer.

The method of the present invention is based on the utilization of a mathematical model of a selected cross sectional shape of a single fiber. Using this mathematical model, and with the fiber cross section oriented in a fixed position, ray trace optics are calculated for a selected number of photons of light as they are assumed to strike the fiber at random. The path traced by each photon arriving at the position of a theoretical observer is determined and its final destination is counted in one of a selected number of discrete windows.

In one embodiment of the invention, the trace optics of 400 photons were used for the fixed fiber cross section and 35 discrete windows were used to count and record the locations of the final destinations of the photons. Each window was 5 degrees wide and centered every 5 degrees around half of a cone of revolution. Thus, the photons of incident light an observer would see were collected discretely and counted in each of the 35 windows.

When the above described scan is completed, the fiber cross section is indexed to a new position, preferably only slightly displaced from the preceding position by an interval of say one degree or so by rotating the cross section of the fiber about the z axis perpendicular to the cross section, and another scan is conducted at the new position in the same manner as that described for the first selected position. Assuming 400 photons were used in the first scan, the trace optics of another 400 photons are calculated for the new position. The process is repeated for successive indexed positions of the fiber cross section until a full 360 degrees of fiber cross section rotation are complete and the selected number of simulated test photons, say 400 as in the example given, are traced at each one degree interval for the example given. The exact manner of tracing the optical paths of the simulated test photons will be set forth in further detail later in the specification.

Figure 2:
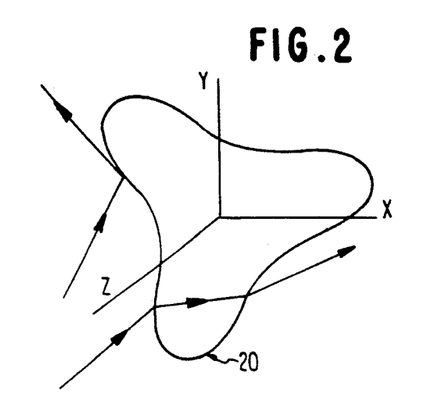
FIG. 2 is a cross sectional view of a representative fiber cross section in orthogonal x,y,z coordinate space.

The mathematical model of the test fiber cross sectional shape may be developed in any one of several ways. FIG. 2 is an illustration of an arbitrarily selected contour 20 of the cross sectional shape of a fiber. The fiber cross section contour 20 illustrated in FIG. 2 is of a trilobal shape and is shown in an x,y,z coordinate format with the z axis being perpendicular to the cross section and coincident with the longitudinal axis of the fiber. As will be later explained in further detail, it is important that the cross section be selected so as to be perpendicular to the longitudinal axis of the fiber. Skewing of the plane of the cross section relative to the longitudinal axis will produce distortions in the apparent cross sectional shape and cause errors in the method of determining luster from such cross sectional shape.

One method of deriving a mathematical model of fiber cross section shape of a contour such as that shown in FIG. 2 involves specifying the x,y coordinates of the shape of the contour. In the case of an actual physical fiber, this can be done by using a photo-micrograph of the actual fiber cross section and then making a digital scan of the actual enlarged image of the cross section. The graph traced in such a fashion has a set of coordinates describing the fiber cross section.

This method for obtaining the x,y coordinates has certain limitations in resolution. Furthermore, the means used to reproduce a cross section from a photo-micrograph is critically dependent on cross sectional geometry. For example, a circular cross section is a trivial case requiring only one variable to graph while a symmetric multilobal shape is more difficult and more error prone.

A second method for obtaining the fiber cross section mathematical model has been formulated as part of the present invention and is therefore preferred. This method has a very high degree of accuracy and is able to reproduce an arbitray multilobal fiber cross sectional geometry. This preferred method uses automated image analysis together with what will be referred to herein as the "Fourier shape descriptor method". Fourier analysis methods are in general well known, as described, for example, in the book "Applications of Discrete and Continuous Fourier Analysis" by Weaver, H. J., published by John Wiley and Sons, New York, 1983, and in a paper entitled "Automatic Dimensional Inspection of Machine Part Cross-Sections using Fourier Analysis", by Etesami, F. and Uicker, J. J. Jr., Computer Vision, Graphics and Image Processing 29 (1985).

The Fourier shape descriptor method used in the present invention is based on the discrete Fourier series transformation of the fiber cross section contour. In the method of the present invention, a one-dimensional function describing the fiber cross section contour is transformed into a discrete Fourier series of numbers which can be calculated in a digital computer. In this way, the frequency content of the fiber contour is determined. For example, in a nearly circular fiber, low frequencies predominate whereas higher frequencies are present in a more complex octolobal fiber.

Representation of a fiber by the frequency content of its cross section permits concise and highly useful characterization of shape. The Fourier shape descriptor method is a completely general approach to the description of a fiber shape.

The method of the invention in one embodiment thereof will be explained with reference to the illustration of FIG. 3, which shows a portion of a fiber 30 having a longituginal axis 32. The illustration is shown in a perspective format with parallel rays of light photons 34 being directed from a source above the fiber and in a direction perpendicular to the horizontal plane 33 above which there is positioned a circular ring 35 of observer sectors such as shown at 36. The fiber 30 is oriented such that its axis 32 is at an angle of 45 degrees to the horizontal plane 33 and also to the direction of the impinging light 34 and at an angle of 135 degrees with respect to the maximum specular reflection angle which forms the plane of the ring 35 and the observer sectors 36. The 45 degree angle orientation of the fiber 30 is chosen for the particular embodiment for the reason that it has been found to approximate the typical average fiber orientation in a carpet on a floor in relation to meaningful impinging light and an observer. Other angular orientations of the fiber may be employed dependent upon the intended orientation of the fiber in actual use and dependent upon the subjective data with which correlation is to be made.

The observer sectors extend over equally spaced intervals or windows 36 around the periphery of the viewing ring which extends around the fiber 30 and are spaced in each case at equal radial distances from the fiber. The observer viewing sectors may, for example, each extend over about 5 degree intervals and, because only scattered light above the carpet plane is of interest, need extend only around a 180 degree half-circle. For the example given, each observer sector extends over an arc of 5 degrees centered every 5 degrees around the half-circle and the observer sector network is thus made up in total of 35 discrete windows in which light photons may be collected after interacting with the fiber 30.

The fiber 30 has a cross sectional shape 40 which is taken on a plane perpendicular to the longitudinal axis 32 of the fiber. As will be explained later in further detail, the cross sectional shape 40 of the fiber 30 is utilized to determine the trace optics of light photons from the source as they interact with the fiber 30. The destinations of the interacting photons are determined by counting the number of photons arriving in each of the observer windows 36 for a selected total number of impinging photons.

In a typical case, a total number of 400 photons was used for each fixed position of the fiber 30 and this was determined to be statistically sufficient for the embodiment described. Only photons arriving at one of the observer window sectors 36 in the horizontal plane are counted. Some of the photons pass through the fiber directly or with internal reflection, and are lost and thus do not contribute to the count.

When the aforementioned process has been completed for one fixed position of the fiber 30, it is rotated a small increment, say one degree, about its longitudinal axis 32, for example in the direction of the arrow 42, and the same process is repeated, in this case for another 400 photons. Then the fiber is indexed another one degree about the longitudinal axis and the same process repeated again and continued until the fiber has been indexed through a full 360 degrees of rotation and 400 photons are traced in each one of the one degree incrementally spaced interval positions. Thus, the fates of 144,000 total photons are traced in the course of an analysis of a single fiber.

Figure 3:
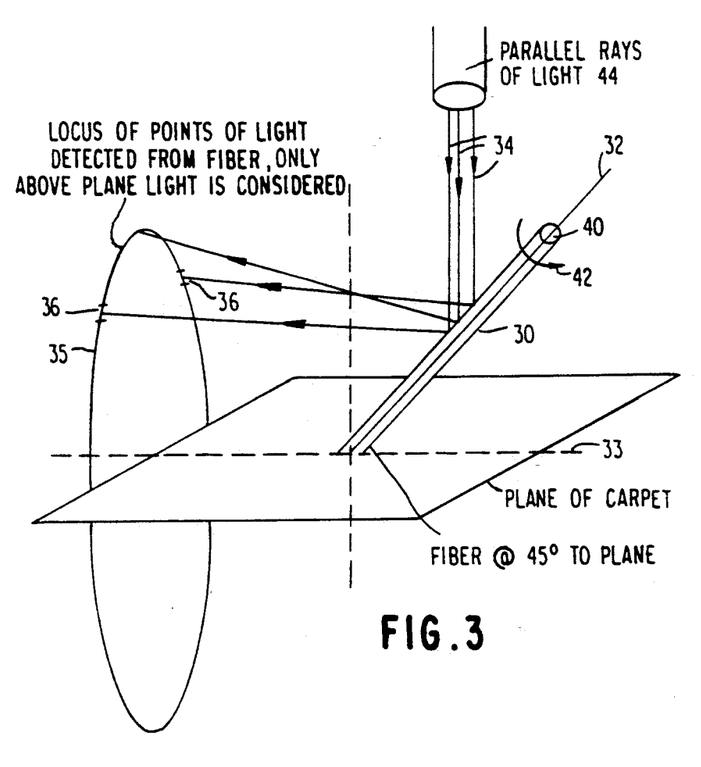
FIG. 3 is an illustration of a conceptual visualization of a fiber filament in relation to simulated impinging light and the distribution pattern thereof after interaction with the fiber filament.

All of the foregoing steps are performed through mathematical calculations, the illustration of FIG. 3 being a visualization of the process. The trace optics of the interacting photons are calculated based on the index of refraction of the material of the fiber and the shape of the cross section taken in a plane perpendicular to the longitudinal axis of the fiber. When the cross sectional shape of the fiber is rotated about its longitudinal axis, a cylinder of interaction 44 with the impinging photons is generated. In other words, only photons within the cylinder 44 can have any interaction with the selected cross sectional shape in any of its incremental positions and the selected count of photons, in this case 400 for each incremental position, are confined to the cross sectional area of the cylinder 44.

The complete scan as just described provides a distribution profile for the destinations of the impinging photons showing the number of photons which have arrived in each of the observer windows 36. This information is then correlated with subjective luster rating data to develop a data base for use as a part of the methodology of the present invention. In other words, particular distribution profiles are correlated with their corresponding luster rating parameters to enable the distribution data to be translated into luster information.

The number of photons collected in each discrete observer window for all 360 orientations of the fiber simulates scattering by a large number of fibers with random orientation. Since the resultant distribution of photons in each window may be symmetric, the data in such case can be simplified by folding the curve around the vertical axis, thereby giving a set of 18 numbers. These numbers are normalized by dividing the number of photons in each pair of windows by the number of photons which would have been found there if the fiber had scattered the photons totally randomly. The normalized numbers typically range from about 0.1 to 1.75, i.e. the amount of light scattered by a particular cross section in a particular direction may be as low as 10% of random scattering or as high as 175% thereof.

For purposes of the embodiment described, the Fourier coefficients were calculated in the manner set forth below. While various Fourier series may be used in the method of the present invention, a preferred Fourier series used is:

$$u(l) = \sum_{n=-N}^{N} c(n)\exp(2\pi i n l/L) \qquad \text{Equation 1}$$

where u(l) is the radius vector in the complex plane, namely:

$$u(l) = x(l) + iy(l), \qquad (2)$$

and x(l) and y(l) are fiber contour points, l is the arc length of the fiber measured counter-clockwise from the initial trace point, L is the total fiber perimeter, the coefficients c(n) are the complex Fourier shape parameters, and $i = \sqrt{-1}$.

From the cartesian contour coordinates x(j),y(j), for j=1 to M, the radius vector and arc length are calculated:

$$l(k) = \sqrt{\{[x(k+1)-x(k)]^2 + [y(k+1)-y(k)]^2\}}, \qquad (3)$$

$$u(k) = x(k) + iy(k), \qquad (4)$$

where k=1 to M, $i=\sqrt{-1}$, and by definition, x(M+1)=x(1) and y(M+1)=y(1). The u(k) are expanded as a Fourier series in Equation 1 which generally converges at some order N.

The Fourier shape descriptors, c(n), n=−N to N, which may include up to 96 coefficients in a preferred method, are calculated as integrals around the fiber contour. These generally complex numbers contain all the size, shape and orientation information about the fiber with N<<M.

In Equation 1, l is a continuous variable with values from 0 to L (the fiber perimeter). By assigning any value to l in this range, values of u(l) are calculated which closely reproduce the fiber contour.

Such a procedure is disclosed, for example, in "Shape Discrimination Using Fourier Descriptors", by Persoon, E. and Fu, King-Sun, IEEE Transactions on Systems, Man and Cybernetics, Vol. SMC-7, No. 3, March, 1977.

Each Fourier shape descriptor is calculated as an integral over the entire fiber contour. The method is general in that any symmetrical or asymmetrical cross section can be analyzed with equal ease. Since representation of the fiber cross section in a Fourier series is equivalent to a "least squares" smoothing of the contour, small artifacts arising in the case of a traced contour are removed mathematically. The convergence of the Fourier series provides an analytical parametric equation that represents the fiber cross section for fiber luster calculations.

The Fourier shape descriptor method works well in describing fiber cross sectional shapes which are of practical interest. In practice, microscope images of fiber cross sections are digitized, the Fourier descriptors determined and then transferred to a computer where the ray trace luster prediction program is resident.

A given fiber cross section is described by a parametric equation, Equation 1 above. Each such equation has a set of Fourier coefficients (typically there are 96 coefficients) which uniquely define the fiber cross section, and from these coefficients an x,y coordinate data file is created in the computer. The x,y coordinate data is a representation of the fiber cross section in a standard form.

The luster prediction starts with the fiber in an arbitrary rotation around its axis. The radius R of the circumscribed cylinder of the cross section is calculated. Next a cartesian coordinate system is defined with the z axis coinciding with the fiber longitudinal axis, which is defined as going through the center of mass of the cross section, and with the origins of the x and y axis lying on the z axis. The starting point of all photons is at −R<x<+R, y<−R, z=0, where x is a random number within the specified interval. The initial path of the photon is described by the column vector Equation 5 as follows:

$$\{s\} = \begin{matrix} 0 \\ (n/2)^{}1/2, \\ (n/2)^{}1/2 \end{matrix} \qquad \text{Equation 5}$$

where n=1 in the typical case, the refractive index of air for a photon of visible light.

A determination is made as to whether a "test" photon will hit the fiber. If not, the test photon is treated as if it never existed (the fraction of photons which miss the fiber ranges from zero for round cross sections to up to a theoretical maximum of 25% for very high MR cross sections). If the test photon hits, the probability is ½ that the photon is polarized parallel or perpendicular to the fiber axis. Polarization determines which of Fresnel's laws apply and whether the photon is reflected or refracted and which refractive index to use in Snell's Law. Once the initial polarization of the photon has been determined (by a coin toss algorithm) this polarization is retained until the photon has permanently left the fiber and its angle of departure is calculated.

When the photon hits the fiber, all points of intersection which it would hit if it proceeded in a straight path are identified and, among those, the one which is closest, and therefore hit first, is determined. This procedure uses a subroutine called HIT which is invoked again in later stages of the program whenever it is necessary to determine whether and where the photon will next interact with an interface. The applicable program steps are disclosed in detail in the Microfiche Appendix which is incorporated herein.

Once the intersection point which is first hit by the photon is identified, Fresnel formulae are used to determine if the photon is reflected or refracted. This can be accomplished, for example, by utilizing event probability statistics at each interface. To evaluate Fresnel's formulae, a calculation of two angles $\theta i$ and $\theta t$ is made. The first involves calculating the surface normal; the latter invoking Snell's Law.

The three points (xi, yi, 0); (xi+1, yi+1, 0) define the tangent plane to the cylinder at a point between (xi, yi, 0) and (xi+1, yi+1, 0). The two unit vectors, {a} and {c}, $$\{a\} = \begin{vmatrix} 0 \\ 0 \\ 1 \end{vmatrix} \text{ and } \{c\} = \begin{vmatrix} (x2-x1)/D \\ (y2-y1)/D \\ 0 \end{vmatrix} \quad \text{Eq. 6}$$

where $D=[(x2-x1)^{}2+(y2-y1)]^{}\frac{1}{2}$ point from the first point to the second and third point, respectively, and lie in the tangent plane and are orthogonal to each other. Their vector product:

$$\{o\} = \{a\} \text{ cross prod. } \{c\} = \begin{matrix} -(y2-y1)/D \\ +(x2-x1)/D \\ 0 \end{matrix} \quad \text{Eq. 7}$$

is a unit vector normal to the surface of the tangent plane.

From the following equation:

$$\{s\} \text{ dot product } \{o\} = \cos \theta i, \quad (8)$$

it follows that if {s} is a unit vector, n=1, then $$\cos \theta i = 0.7071.(x2-x1)/D. \quad (9)$$

Similarly, it follows that:

$$[\{s\}\text{cross prod.}\{o\}]^2 = n^2.\sin^2 \theta i, \quad (10)$$

and that $$\sin \theta i = \sqrt{\{1-\frac{1}{2}.(x2-x1)^2/D^2\}} \quad (11)$$

This result could have been obtained from Equation 9, but it is given here to illustrate it as an alternative formulation of Snell's Law. Snell's Law can be written as:

$$\{s\} \text{ cross prod. } \{o\} = \{s'\} \text{ cross prod. } \{o\}, \quad (12)$$

where {s} is a vector in the direction of the entering ray whose length is equal to the refractive index of the first medium (n=1 since the photons are traveling through air) and {s'} is a vector in the direction of the refracted ray whose length is equal to the refractive index of the second medium (the fiber interior). In view of Equation 10 and analagous Equation 13:

$$[\{s'\}\text{cross prod.}\{o\}]^2 = n'^2.\sin^2 \theta t, \quad (13)$$

Equation 12 is fully equivalent to the more familiar form of Snell's Law:

$$n.\sin \theta i = n'.\sin \theta t \quad (14)$$

Since Equation 15 follows from Equation 12:

$$[\{s'\}-\{s\}] \text{ cross prod. } \{o\} = 0, \quad (15)$$

the angle between $[\{s'\}-\{s\}]$ and $\{o\}$ must be zero. Therefore:

$$[\{s'\}-\{s\}] = r \text{ dot prod. } \{o\} \quad (16)$$

Now, multiplying both sides of Equation 16 by {o}, and since {o}dot prod. {o}=1, we get, in view of Equation 8, Equation 17:

$$\Gamma = \{s'\}\text{dot prod.}\{o\} - \{s\}\text{dot prod.}\{o\} \quad \text{Eq. 17}$$
$$= n' \cdot \cos\theta t - n \cdot \cos\theta i$$

Substituting into 17 the expressions in Equation 18:

$$n'.\cos \theta t = \sqrt{[n'^2-n^2+(\{s\}\text{dot prod.}\{o\})]^2}, \quad \text{Eq. (18)}$$

we obtain Equation 19:

$$\Gamma = \sqrt{[n'^2-n^2+(\{s\}\text{dot prod.}\{o\})^2]}\{s\}\text{dot prod.}\{o\} \quad (19)$$

Therefore, we find the direction of the refracted ray is given by Equation 20:

$$\{s'\} = \{s\} + r \text{ dot prod. } \{o\}, \quad (20)$$

where r is given by Equation 19.

Now, $\sin \theta t$ and $\cos \theta t$ are given by the fully general expressions:

$$\sin \theta t = (1/n').\sqrt{[n^2-(\{s\}\text{dot prod.}\{o\})^2]} \quad (21)$$

$$\cos \theta t = (1/n').\sqrt{[n'^2-n+(\{s\}\text{dot prod.}\{o\})^2]} \quad (22)$$

where n is the refractive index for the incident ray and n' is the refractive index for the refracted ray.

The computational method used in the FORTRAN program uses the following equations:

When in air

| | |
|---|---|
| $\cos\theta a = \{s\}\text{dot prod.}\{o\}$ | Eq. 23 |
| $\sin\theta a = \sqrt{[1-\cos^2\theta a]}$ | Eq. 24 |
| $\sin\theta f = (1/nf) \cdot \sin\theta a$ | Eq. 25 |
| $\theta f = \sin^{-1}(\sin\theta f)$ | Eq. 26 |

When in the fiber

| | |
|---|---|
| $\cos\theta f = (1/nf) \cdot \{s\}\text{dot prod.}\{o\}$ | Eq. 27 |
| $\sin\theta f = \sqrt{[1-\cos^2\theta f]}$ | Eq. 28 |
| $\sin\theta a = nf \cdot \sin\theta f$ | Eq. 29 |
| $\theta a = \sin^{-1}(\sin\theta a)$ | Eq. 30 | where the subscripts a and f refer to air and fiber, respectively.

Having calculated the angles $\theta i$ and $\theta t$, the probability of the photon being reflected or refracted is calculated using the appropriate form of Fresnel's law for the previously determined state of polarization of the photon. These are Equation 31 for parallel polarization and Equation 32 for perpendicular polarization:

$$R_{par} = \frac{\tan^2(\theta i - \theta t)}{\tan^2(\theta i + \theta t)} \; ; \; T_{par} = 1 - R_{par} \quad \text{Eq. 31}$$

$$R_{perp} = \frac{\sin^2(\theta i - \theta t)}{\sin^2(\theta i + \theta t)} \; ; \; T_{perp} = 1 - R_{perp} \quad \text{Eq. 32}$$

If refraction occurs, then the new path of the photon is determined by Equations 19 and 20. If reflection occurs, then:

Eq. 33 $\sin \theta_{i'} = \sin \theta_1$; $\cos \theta_{i'} = -\cos \theta_i$, and thus, Eq. 34 $\Gamma = -2n.\cos \theta_i = -2.\{s\} \text{dot prod.} \{o\}$, and $$\{s'\} = \{s\} + \Gamma\{o\} = \{s\} - 2.(\{s\} \text{dot prod.} \{o\}).\{o\}. \quad (35)$$

Unless a test photon has left the fiber for good, which means subroutine HIT failed to locate a point of intersection in its path, the photon path followed is determined using Equations 23, 24, 25, 26, 31, 32, 19, 20 and 35. This approach allows a photon to exit from one lobe of a multilobe cross section and reenter another lobe.

Next, a test for sign of the y component of the unit vector describing the path of a photon is made. If the sign is positive, the photon is assumed to be lost to an observer according to this model. On the other hand, if the y component of this unit vector is negative, the photon returns the observer and is collected in one of the 35 discrete windows according to the x component of the unit vector.

For each of 360 different orientations of the fiber, spaced in increments of rotation of one degree about the z axis, 400 test photons are generated so as to strike the fiber at random from the left edge to the right edge of the fiber. After all 400 photons have been traced, collected photons in each observation window are counted as well as the number of photons which miss the fiber. As stated above, the fiber is indexed in one degree increments and the process repeated until the fiber has been rotated completely about the z axis.

The present method uses a Fourier series with up to 96 parameters fitted to the edge points of the fiber cross sectional shape. The degree to which the fiber contour is matched depends on the convergence of the series in each case. In general, a smooth shape retaining all of the significant shape information is obtained from the Fourier shape descriptor method. Any graininess in the original representation, such as in a video image for example, is smoothed out by this process. In addition, the Fourier parameters are real values and the x,y data generated from the Fourier sum are real valued, thus overcoming the resolution or "pixel noise" problem encountered in an integer x,y description and thereby enabling a more accurate luster calculation.

In order to correlate the sets of 18 numbers generated in each case with fiber luster, empirical ratings were used. Photomicrographs of 21 cross sections of fibers were obtained. Six typical filaments were selected from each photomicrograph and photographically enlarged to about 6 to 8 inches in diameter. Enlarged photos were then digitized using a digitizing tablet and these data files were then Fourier transformed. The 21 selected cross sections were taken from carpet fibers which were used in the construction of both level-loop and cut-pile carpets. These carpets were rated by a panel of experts for both bulk and luster on a scale of from 0 to 20.

Luster is known to depend inversely on bulk. Therefore, a correlation between subjective luster as the dependent variable and subjective bulk and a transform of the number of photons collected by each window as the independent variables is established in accordance with one method embodying the present invention. It was found that the averages of the subjective ratings for the level-loop and cut-pile carpet constructions were highly correlated and thus provided a reliable data base for the method of the invention. The best correlation with the numbers of photons collected in each window was by weighting with the square of the angle from the floor, i.e. those photons which come from directly underfoot were given 4 times as much weight as those that are observed at a 45 degree angle and 9 times as much as those observed at a 30 degree angle above the floor. The correlation equation so determined is Equation 36:

$$LUSTER = 1.64 + 9.02B + 7.74C - 0.396(bulk) \quad (36)$$

where,
LUSTER = average subjective luster rating of level-loop and cut-pile carpets
B = BRIGHTNESS
C = CONTRAST
bulk = average subjective bulk rating of level-loop and cut-pile carpets "Brightness" is, in general, a measure of how many photons come back toward the observer, and uses an angle weighted sum over the range of filament orientations of the number of photons in each window. "Contrast" is a measure of how the photon distribution changes as fiber orientation changes, that is as a function of fiber rotational orientation. Other parameters that take into account the total distance traveled by the photons in the fiber can also be used as predictors of dye yield. Various other parameters can also be utilized and correlated with subjective data.

The above equation 36 was found to be accurate within an error range about the same as the reproducibility of the subjective ratings. Thus, Equation 36 is a very good predictor of subjective luster.

The luster properties may be calculated in accordance with the method of the present invention as described above with less computational intensity using the methods described and claimed in copending U.S. patent application entitled "METHOD OF MODELING A COMPUTATIONALLY INTENSIVE ALGORITHM USING A PARALLEL DISTRIBUTED PROCESSING NETWORK", filed in the names of Thomas W. Lynch and Aaron J. Owens on the same filing date as the present application and assigned to the same assignee as the present application, the subject matter of which is incorporated herein by reference.

Another aspect of this invention relates to a method for deriving the cross sectional shape profiles of physical fibers which are in the form of a cluster of touching fiber filaments such as in a thread line or a yarn. When a fiber is in the form of an individual filament, a cut can be made through the fiber perpendicular to its axis and the cross section scanned for the purpose of deriving a mathematical representation of the cross sectional shape. When the fibers are bunched together as in a thread line, however, which may have as many as 100 or more individual fiber filaments, many of which are held together in a touching configuration, cross sectioning to isolate a single fiber filament for analysis in the manner described above is very difficult, thereby making manufacturing control of fiber cross section correspondingly very difficult.

The imaging methodology of the present invention provides a solution to this problem and permits the coupling of luster determination and control with manufacturing control of fiber cross section. The present invention thus includes a method for analyzing the image of a cross section of multiple touching filaments of fiber and deriving therefrom the contour of a single fiber without the necessity for separating the fibers and isolating a single fiber for analysis.

Figures 4, 5:
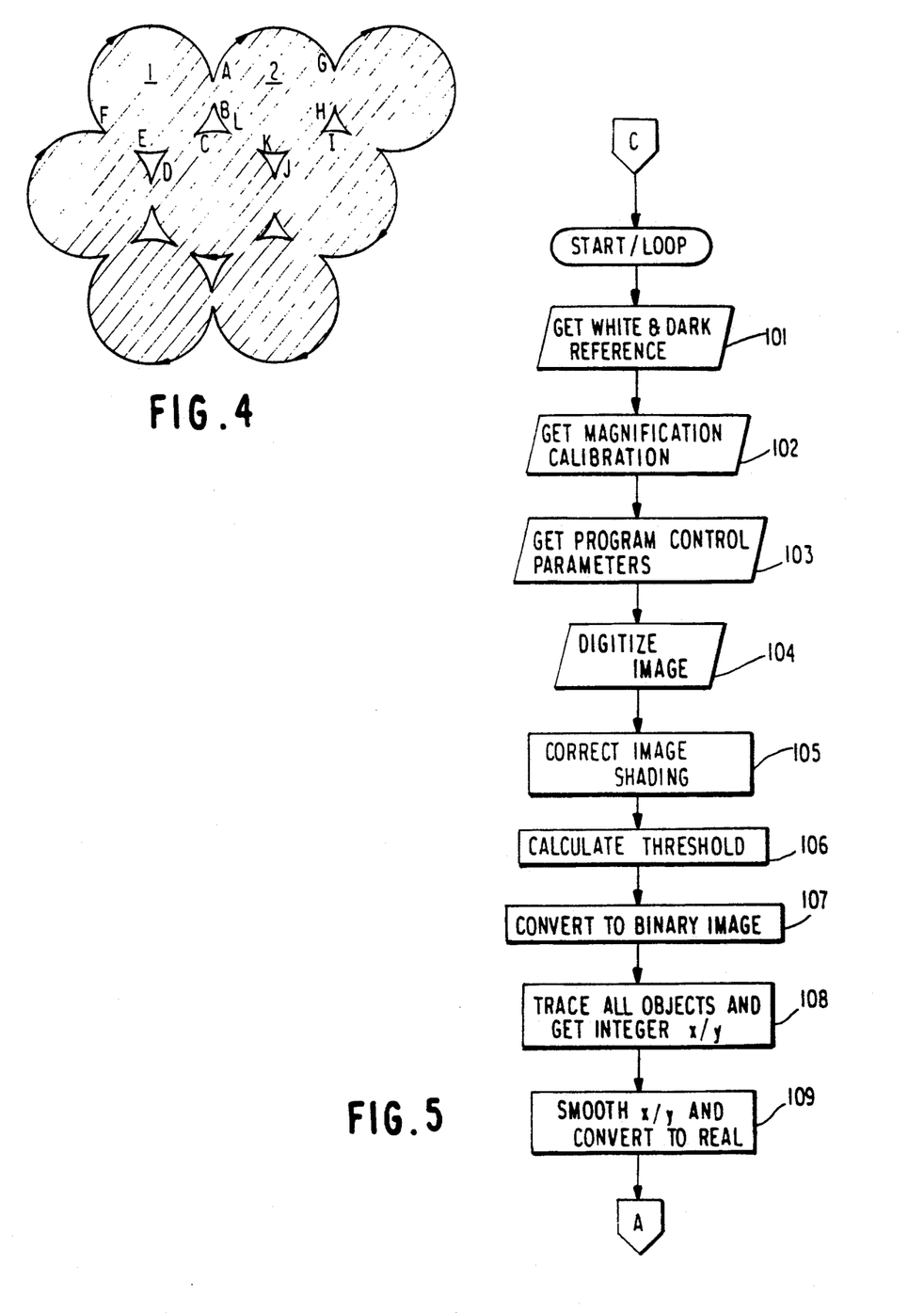
FIG. 4 is a representation of an image of a cross section of multiple touching fiber filaments in a group.
FIGS. 5, 6, and 7 are flowcharts of one embodiment of the invention for determining the individual contour shapes of a plurality of touching objects, such as fiber filaments, in a touching group configuration.

FIG. 4 shows the cross sections of a group of touching fiber filaments such as may be twined together, for example, in a thread line or a yarn. In order to obtain a physical cross section of such a group along a plane perpendicular to the axes of all of the filaments, the bundle of filaments is first dyed with a suitable dye, such as Tectilon Blue 2GA acid dye, and then stretched longitudinally to remove yarn crimp and align the filament axes and thereby orient all of the filaments in a parallel relationship. Next, the stretched and parallel positioned yarn bundle is embedded in an epoxy resin of matching refractive index to the material of the filaments, cured and microtomed in a plane perpendicular to the filament longitudinal axes. The resulting thin section of the fiber bundle appears as illustrated in FIG. 4 when enlarged under microscopic examination.

A method of preparing such a cross sectional image is disclosed in copending U.S. patent application Serial No. 443,372, entitled "METHOD FOR CROSS-SECTIONING CRIMPED YARN SAMPLES" filed in the name of Robert Hempton on Nov. 30, 1989, and assigned to the same assignee as the present invention.

In order to obtain a high contrast between the video image of the blue dyed fiber bundle and the background, a red interference filter (for example, Ealing #35-3896 with 630 nm wavelength and 10.9 nm bandwidth) is used on the microscope with the video camera. The resulting image is of high contrast and all portions of the image of the thin sectioned fiber bundle appear dark on a light background.

An image of the multiple cross section is then prepared, such as by means of a photomicrograph of the cross section, so that it can be enlarged and used for purposes of making a digital scan of the multiple cross section image. The image so produced is of the general format shown in FIG. 4 in which the cross sections of the individual filaments are in a touching relationship. Only a portion of the total image is illustrated in FIG. 4.

The video image of a microscopic view of a yarn bundle cross section prepared as above is easily digitized using commercial video frame grabbers and computer software to handle image format data arrays. The image so produced is of the general form shown in FIG. 4 in which the cross sections of individual filaments touch each other at points on their periphery. Only a portion of the total image is illustrated in FIG. 4, the entire image of the yarn bundle or some small number of individual filaments being selectable by changing the magnification on the microscope.

Figure 6:
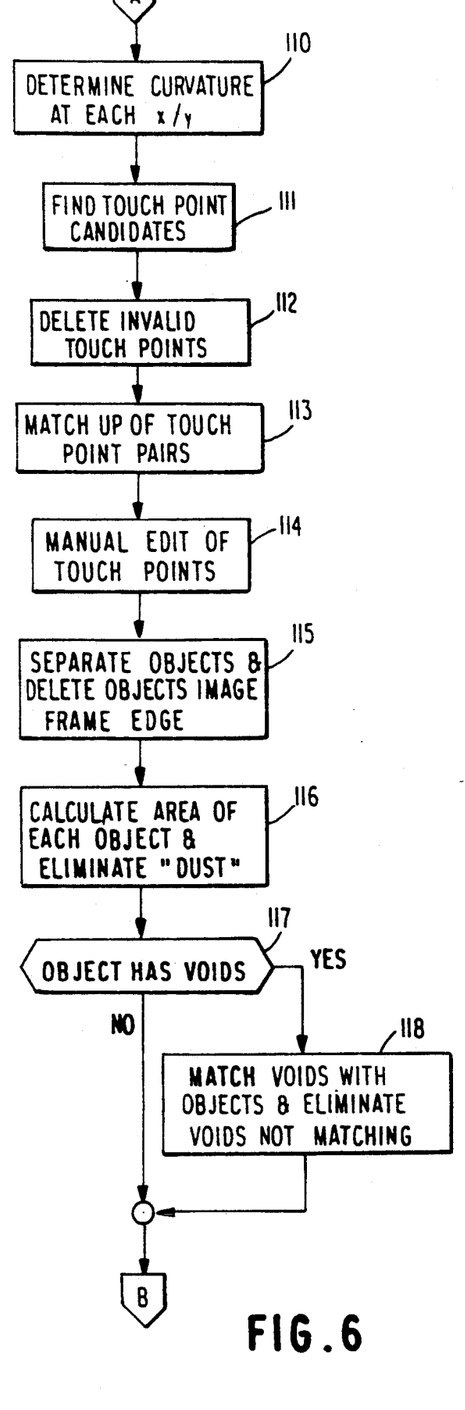
Figure 7:
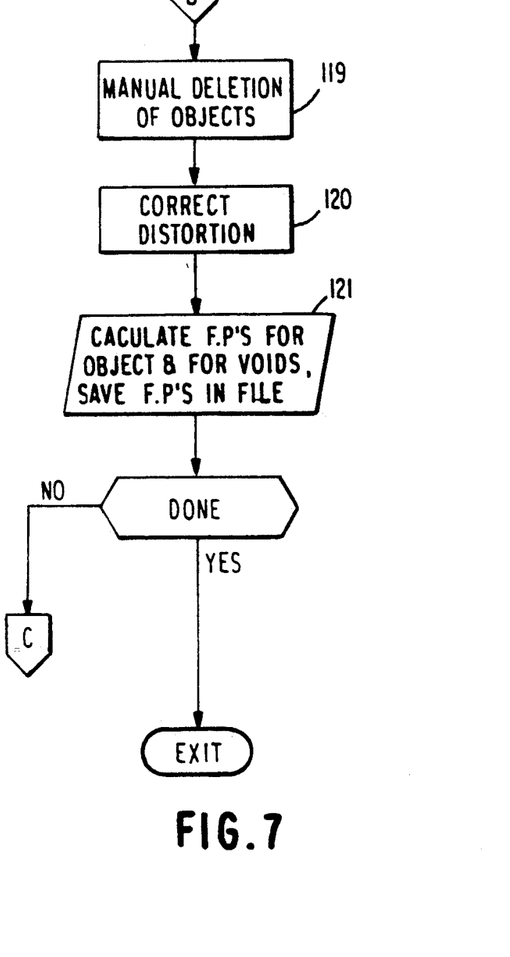

After the cross sectional image of the fiber bundle is prepared in the format of FIG. 4, the image analysis method of the present invention is used to derive from the multi-filament touching image the individual cross sectional shapes of the single fiber filaments. The flowchart for one embodiment of the method is shown in FIGS. 5, 6 and 7. The implementing computer program therefor is disclosed in the Microfiche Appendix referenced above which is incorporated herein by reference.

A detailed discussion of the flowchart will follow later. First, a discussion of the image anaylsis method of the present invention will be presented with reference to FIGS. 8 through 11.

In many measurement applications of image processing, the image contains particles or objects that are touching. In such cases, it is difficult to measure individual object properties (size, shape, etc.) since the boundary between touching objects is not observed. In some cases, it is possible to use image separation methods to isolate non-touching images and, where that is possible, such techniques may be used with the above described methods of the present invention.

However, in prior art methods, if touching of adjacent shapes is not explicitly accounted for, each conglomerate of shapes is counted as one object whose area is the sum of the areas of the objects in the conglomerate and whose shape is the shape of the conglomerate. More information is yielded in another approach which uses global binary image processing techniques to separate touching images. It results, however, in a significant loss of object size and shape information, i.e. these properties are modified in the separation process. Commercially available apparatus is available for particle size analysis based on such an approach.

The present invention employs a novel approach which can separate touching objects while substantially retaining the size and shape information of each object. This method is based on a geometrical analysis which uses the points in the image where the objects touch. These touching points always occur in pairs, with one point on each side of a touching area.

Figure 8:
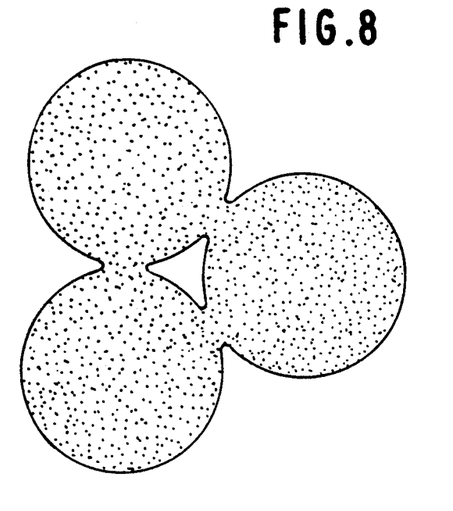
FIG. 8 is an image representation of a grouping of black circles on a white background which is used for purposes of explaining certain aspects of the present invention
Figure 9:
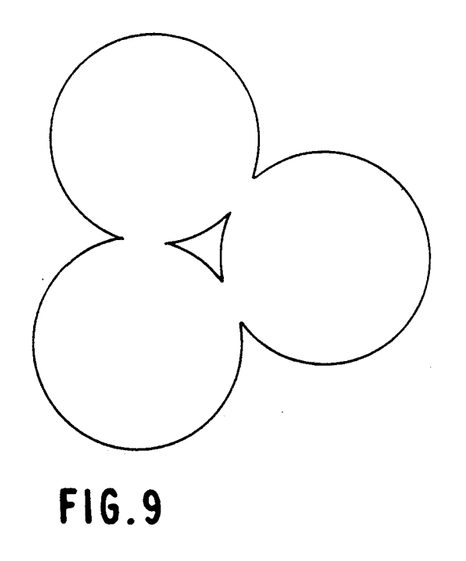
FIG. 9 is a representation of one embodiment of the method of tracing fiber filament peripheral contours for purposes of separating individual cross sectional shapes.

As an example, consider an image of black circles on a white background as shown in FIG. 8. When the objects touch, there is a common black area between the objects with no apparent boundary. On each side of this area there are touching points. These touching points are automatically located and matched up into pairs and then the objects are separated. For each of the touching objects, the missing part of the contour in the touching area is mathematically generated based on information to either side of this area.

Because of the variety of artifacts which can intrude into an image, some manual image editing may be provided. For yarn cross sections, these artifacts can include dirt, out-of-plane fibers, overlapping fibers and fibers distorted in the cutting process.

In the method of the present invention the yarn may first be dyed if it does not itself provide an image of sufficient contrast. The yarn is then cross sectioned, preferably in the manner described above, and mounted on a microscope slide. The slide is placed in a microscope, the image is focused and a field is selected for analysis. The program is then started.

A threshhold is automatically calculated which is used to convert the image to a binary or on-off image representation to distinguish objects from the background (as, for example, FIG. 8). Ideally, circles should touch at only one point. In practice, image resolution and any threshholding technique are not perfect and touching areas tend to get exaggerated. Thus, there is a touching area between objects, rather than just one point in common. All thresholded objects, whether isolated or conglomerates, are automatically traced (as in the tracing of FIG. 9) and the contour coordinates are retained. The parts of the analysis up to this point are known in the prior art.

The program is controlled by a file previously set up for the fibers to be analyzed. This file contains several adjustable parameters which can be fine-tuned to different general types of samples and operating conditions (i.e. circular fibers, trilobal fibers, low magnification, high magnification, etc.). In practice, the parameters have similar values for all samples. Using these parameters and the contour coordinated, the program locates the touching points by calculating the two-dimensional curvature at all points along the contour. Points which are suitably above a preselected curvature threshhold value are identified as touching points. Several test conditions are included in the program to distinguish valid touching points from spurious points which happen to have high curvature.

Figure 10:
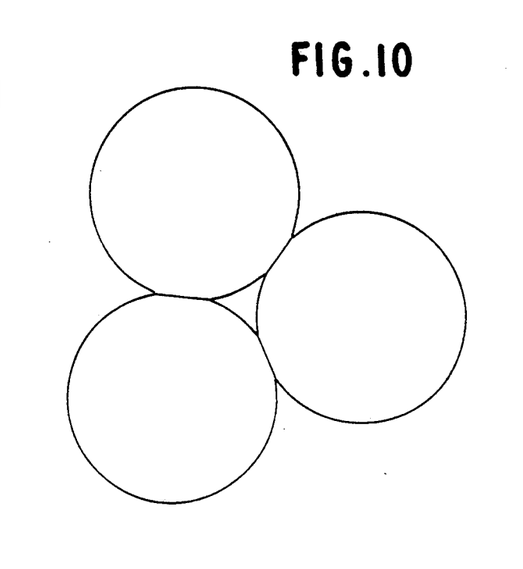
FIG. 10 is an illustration of the touching objects in matching point pairs.

The program then matches up the touching points into pairs. This is displayed by connecting the touching point pairs with straight lines as illustrated in FIG. 10. If desired, the results may be manually edited, that is improper connections can be broken, unmatched points can be connected, extraneous touching points can be eliminated or required touching points created.

A program algorithm then goes through the image and extracts each individual object. The processing is independent of the particular configuration of the touching image, i.e. it does not matter whether given object is isolated, touching one other object or touching several other objects. It is also independent of the shape of each object within normal ranges of operations.

Figure 11:
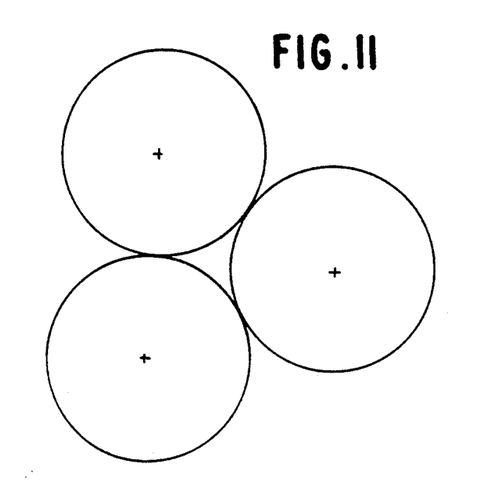
FIG. 11 is an illustration of the separated individual contour shapes.

The missing contour segments (in the touching areas) are then interpolated using a polynomial function fitted to the parts of the contour before and after the touching area. Additionally, the straight line data between the touching points is used in the fit, with a lower weight, to help guide the fit. This allows for a close approximation to the actual missing segment as illustrated in FIG. 11 showing the extraction of each object (illustrated with highlighted centers) and the interpolation of the missing contour segments.

At this point, the final results are displayed. There is another opportunity for manual image editing in that an fibers which are not appropriate to include in the measurements can be eliminated.

Shape parameters are calculated for each fiber and a data file containing these parameters is created for each fiber. The file names are automatically incremented from a root name input at the beginning of the program.

The files are submitted to the ray trace method program as described above and the luster properties are then calculated for each fiber. The spread of luster properties for the fibers in the cluster can then be determined.

The following is a description of the major steps as shown in the image analysis flowchart shown in FIGS. 5, 6 and 7. Each step in the flowchart is labeled with a description of the step which it represents.

Referring to steps 101 and 105 of FIG. 5, whenever a simple image threshold value is used, greater accuracy results when a correction is done for any shading in the image due to non-uniform illumination and/or variation in response at different points in the camera sensor. For this purpose, white and dark reference images are acquired and stored at the beginning of program operation. After a cross section image is located and focused, and the light level is set, the white reference is obtained by moving the cross section out of the field of view so that a clear area of the cover slip is in the field of view. Frame averaging (typically 64 frames) is used for best results. The dark reference is obtained by diverting the light from the camera sensor and frame averaging (typically 64 frames). References are sampled periodically. Shading correction techniques are known in the literature.

With respect to step 102, a microscope reticle with circles of known diameter is used to determine the calibration factor. i.e. the number of microns in the cross section image that correspond to one pixel in the image. For camera/video digitizing board combinations which result in so-called "square pixels", the calibration factor is the same in the x and y directions. For systems with so-called "non-square" pixels, the calibration factors are different in the x and y directions and both factors must be used to correct the shape of traced filaments. The treatment of non-square pixels is well known in the industry.

With respect to step 103, several parameters are used in the program, e.g., one such parameter specifies the number of contour points to include in a particular least squares fit. A contol file stores these parameters. Although the nominal values of these parameters work well for a wide range of shapes, the values may be fine-tuned for particular shapes and magnifications. Such a set of particular parameters is associated with a "fiber name". The control file can contain several such fiber names with their associated set of parameters. The set of parameters includes:

Root Filename—root name used for Fourier parameter files. The program automatically assigns names to files by adding numbers, in sequence, to the root name.

Fourier Series Order—the highest order used in the Fourier series which represents the filament shapes (the outer filament contour in the case of voided filaments). 12 is a typical value; 24 is the largest ever needed in known applications of the present invention.

Voided Filament Flag—used to indicate to the program that voided filaments are present.

Voided Fourier Series Order—the highest order used in the

Fourier series which represents the void shapes, typically 6.

Dust Size—the pixel area below which a traced object is considered dust and removed from the image data, typically 700.

Void Threshold Area—in tracing filaments, the outer contours are trace in a sense opposite to that of voids and inclusions between filaments. The calculated pixel areas are of different sign if the tracing is done in a different sense. In the present invention, voids and inclusions have negative area. This parameter (a positive number with units of pixel area) is used for negative area objects. If the absolute value of the pixel area is below the value of the parameter, then the object is considered a void. If the absolute value of the pixel area is above the value of the parameter, then the object is considered an inclusion. The different treatment of these two classes of objects is considered below in reference to the location of touching point candidates. A typical value is 1200.

Curvature Threshold—the threshold curvature value in the location of candidate touching points, typically 0.2.

Curvature Run Length—specifies the minimum number of points which must be above the curvature threshold to be condidered a candidate touching point region, typically 2.

Interpolation Fit Points—the number of contour points both before a given touching point and ahead of its matched touching point, including in both cases the touching points themselves, to use as data for the calculation of the interpolation curve which fills in filament contour data in the touching regions, typically 15.

Interpolation Fit Degree—the highest degree polynomial used in the interpolation fit, typically 4.

Weighting Factor—matching touching points are initially connected with a straight line. In doing the interpolation curve fit, the straight line data is included with the contour data before and after the touching points but each straight line data point is weighted by this factor. A typical value is 0.15.

Threshold Method—used to select one of four possible threshold methods as outlined below.

Threshold Number—the fraction of the difference between the grey levels of fiber and background histogram peaks to be added to the fiber peak grey level in the calculation of an image threshold according to one of the methods listed below, typically 0.5.

Delete Test No. 1 Fit Points—the number of contour points both before and after a given touching point candidate, including in both cases the candidate point, used in a least squares fit to determine the tangent vectors at the candidate point due to data before and data after the point. These tangents are used in a test to delete touching point candidates which are not true touching points, e.g., they may be due to dirt on the filament contour. A typical value is 10.

Delete Test No. 1 Fit Degree—the highest degree polynomial used in the Delete Test No. 1 fit, typically 2.

Delete Test No. 1 Angle (deg)—specifies the angle used in the Delete Test No. 1: if the angle between the tangents is greater than this value, the candidate test point is removed from the data set. A typical value is 125 degrees.

Auto-Match Fit Points—the number of contour points both before and after a given touching point, including in both cases the touching point, to be used in a least squares fit to determine the tangent vectors at the touching point due to data before and data after the point. These tangents are used in an algorithm to automatically locate the matching touching point, i.e. the touching point at the opposite side of the touching region. The Delete Test No. 1 Fit Degree is also used here as the least squares fit degree. A typical value is 10.

Search Angle Increase—specifies the amount of degrees by which the angle between the two tangents calculated in the Auto-Match procedure is increased in order to facilitate location of matching touching points, typically 50 degrees.

Delete Test No. 2 Fit Points—used to locate two points for each touching point candidate, between which a straight line is drawn. The first point is found by going this number of contour points before the touching point candidate; the second by going this number of points after the touching point candidate. The points along the straight line are tested to determine whether thay are in fiber or in background. A typical value is 10.

Match Test Fraction—when two touching points are provisionally matched, the image data along a straight line which connects the two points is inspected and if the fraction of such points that are in fiber is less than this value, the match is not made. A typical value is 0.5.

With respect to step 104, each cross section video image is digitized. Frame averaging is used to improve the signal to noise ratio. The particular video image processing boards used to provide frame averaging is a hardware feature.

Referring to step 106, a grey level is calculated for each image. This calculation makes use of the image histogram as is well known in the literature. There are generally two prominent peaks in the histogram, one due to the fiber and the other due to the background. The latter peak is centered at a higher grey level in the usual implementation as the background is bright and the filaments are dark. If the system were analyzing clear filaments on a dark background, (in the case of voided filaments the voids must be made to appear dark in the same manner as the background) the relative location of the two peaks would be reversed and the following discussion would be modified in an obvious way.

The two peaks are located and then the threshold is calculated in one of several ways. Typically it is found as follows. The minimum value of the histogram between the peaks is found. This minimum value may occur at more than one grey level. The lowest grey level at which the minimum occurs is used as the threshold. Other methods of calculating thresholds may also be used: the average value of all grey levels which have the minimum histogram value, the average value of the grey levels of the two peaks, a grey level which is found as the grey level of the fiber peak plus a fixed, specified fraction of the grey level difference between peaks. All of these methods give substantially the same results (as would many variations of these methods) as the preparation of the sample by dyeing and the use of an optical filter in the microscope consistently lead to high contrast and image histograms which show the expected distribution of grey levels.

With reference to step 107, having calculated an intensity threshold, the grey level image is converted to a binary image: all pixels below the calculated threshold are considered to represent yarn material and are assigned one grey level value, e.g., 255; all pixels above the calculated threshold are considered to represent the background and are assigned another grey level value, e.g., 0. The tracing and image separation procedures are all done using this binary image. It is not necessary to actually create a binary version of the image—one could process the grey level image and test each pixel for whether it is above or below the threshold and proceed accordingly.

With respect to step 108, all binary objects representing yarn material in the image, whether isolated filaments or a group of touching filaments, are then traced, i.e. the contour x,y coordinates are found. In a current embodiment, the coordinates retained in the data represent a tracing along the outside of the filament contour, i.e. they are not at threshold points but one pixel away from the corresponding boundary thresholded point. Other methods are possible. It is to be noted that these x,y values are integers. The tracing of binary objects is well known in the art and any suitable algorithm which generates the coordinates along the contours may be used provided, as is usually the case, the tracing of voids and inclusions between filaments is done in an opposite sense to the tracing of other contours. Use of this feature is made in the separation of touching filaments (below). Devices are also available which can do the tracing of binary objects in hardware.

A frame with grey levels equal to that of the background, typically 2 pixels wide, is drawn around the image. This facilitates the handling of objects which touch the border as these can now be traced completely around, independent of the characteristics of any particular frame buffer hardware/software system.

Referring to step 109, in preparation for the calculation of curvature values at each x,y contour point, a smoothing of the coordinate values is done. This is accomplished using an average of x-coordinates and, separately, an average of y-coordinates, both over a smoothing window of adjustable length, typically 3 or 5. Various weightings of points within the window may be used, many of which give substantially the same results. The original integer x,y values are replaced by the smoothed x,y values. These latter values are real-valued.

With reference to step 110, points in the image where filaments touch may be distinguished by the fact that they generally have larger values of curvature than other points in the image, including for example those at the tips of trilobal filaments. The curvature is calculated at each point on each contour. For a curve in space, the curvature is defined as the absolute value of the rate of change of the inclination angle of the tangent line with arc-length along the curve. For a curve represented by parametric equations x=f(t) and y=g(t), the well known equation for curvature is:

$$K = \frac{[(dx/dt)(d^2y/dt^2) - (dy/dt)(d^2x/dt^2)]}{[(dx/dt)^2 + (dy/dt)^2]^{3/2}}$$

In terms of the discrete coordinate variables of filament contours, derivatives are replaced by differences (subroutine TAKE DERIVATIVE).

In step 111, a search is made along each contour for runs of curvature values which are above the selected curvature threshold. The length of the run and the value of the curvature threshold are input from the control file. In each such run of points, the point with the largest value of curvature is stored as a candidate touching point; in the case where all curvature values in a run are the same, the center point in the run is used as the candidate touching point.

In the case of filaments with voids, we do not want to locate any touching point candidates on a void; although the voids may have sharp features, they do not in general touch. Voids, like inclusions between filaments, are traced in a sense opposite to that of the outer filament contour and hence have areas with different signs; in our case their areas are negative. The Void Threshold Area control file parameter is used to distinguish voids from inclusions. For voids, the touching point candidates are not selected on the contour; for inclusions, the touching point candidates are selected. It is to be noted that, if necessary, other criteria, e.g., shape, could be used to differentiate voids from inclusions in a particular application.

Referring to step 112, several criteria are used to test candidate touching points to determine if they are valid touching points. In this connection, reference is made to Delete Test No. 1 and Delete Test No. 2 above. For the latter test, at least some fraction, set typically at 0.5 in the program, of the points along the straight line must lie outside of fiber for the touching point to be considered valid. With fibers, invalid touching points can arise for example if there is a dust particle on the contour. In most cases, the above tests will automatically eliminate such invalid touching points from consideration.

A limitation of these automatic tests, for general applications with non-fiber images, is that sharp contour features located in a valley along a contour cannot be distinguished from valid touching points. A example would be in amages of gears, where the points on the teeth closest to the gear center would have the above characteristics. In any case, if the automatic match-up routine (below) does not find an appropriate match, the point will be automatically eliminated from consideration. Also, manual editing to remove the point is always possible. Finally, it may be possible in specific applications to add additional criteria for validity for touching points, e.g., a test of the distance between matched touching points, which would help to improve the automatic operation of the program.

With reference to step 113, points before each touching point and including the touching point are used to do at least squares fit for the calculation of a tangent vector at the touching point. Similarly, points after each touching point and including the touching point are used to do a least squares fit for the calculation of a tangent vector at the touching point. The Auto-Match Fit Points parameter specifies the number of points to use in the fits. These two tangent vectors, from data before and after the touching point, have some angle included between them. The Search Angle Increase parameter specifies the angle by which this included angle is increased in order to facilitate location of a matching touching point. For each touching point, the other touching points are polled and the best match is determined as the nearest one which is within the angular opening of the vectors of the touching point being matched.

A touching point table is generated. Each item in the table has a pointer to indicate which contour array it is part of, the subscript that it has in that array and another pointer to indicate with which other touching point in the table it is matched. Tests done in the automatic matching procedure guarantee that a given touching point is not matched to more than one other touching point.

Referring to step 114, provision is made for manual editing of the matching of touching points using the touching point table generated in the automatic matching procedure. The operator of the program can do the following: create new touching points where none were automatically found, delete invalid touching points and modify the connections between touching points. The program does not allow a given touching point to be matched with more than one other touching point. If a manual match using an already matched touching point is done, the original match is broken.

With reference to step 115, simply matching touching points does not solve the problem of separating touching filament images. This is because in going from one touching point to its matched touching point, the contour at the matched point branches into two paths. Each path could lead to further touching points pairs with subsequent contour branching. In an image with many filaments that touch, in possibly more than one place on each filament, the number of possibilities is large. Assuming that all touching points have been located and matched, manually if necessary, a key algorithm is now used to extract each touching filament from the image. Any contour with an unmatched touching point is deleted from the data.

In addition to the touching point table described above, a trace table is used to separate touching filaments. This table includes x,y data for all of the contour segments, stored in the order in which each segment was encountered in the original trace of the image. Along with each x,y pair, a flag indicates whether the point is a touching point.

In the tracing of all touching and isolated objects, all contours are traced in one sense, say, clockwise, and all inclusions are traced oppositely (voids would be traced in the same manner as inclusions). Any contour segment which touches the (reduced) image border is eliminated from the data. An isolated filament is recognized by the absence of touching points on its contour.

FIG. 4 represents an example of several touching round filaments. We start at the first touching in the touching point table, say, point A. This gives the first x,y pair of a new array which represents a separated filament. Then the x,y pair of the touching point with which A is matched, in this case B, is added to the separated filament array. Separated filament array data points between A and B are interpolated using x,y data from the straight line which connects A and B. The number of interpolated data points is based on the distance from A to B in units of pixels, typically 1 data point per pixel. Knowing which array B ia a part of, and knowing B,s subscript in that array, data points are added to the separated filament array by incrementing the subscript value of the array that B is a part of and using the corresponding data points. This is continued until a next touching point is encountered, in this example, point C. Data is addedd to the separated filament array by going to C's matching touching point, D, and interpolating straight line data as before. This process continues in this way, going from E to F, until the starting point A is again reached. When this occurs, the coordinates of the filament 1 have been extracted.

Each touching point is used once as the first of a pair of matching points. Thus, the next unused touching point in this example would be B. It is matched with A etc., which takes us around filament 2, thus extracting its coordinates. In this way, each filament may be extracted.

Separation of filaments results in filament shapes which have touching points connected with straight line segments. In order to obtain a better representation of the filament shape, an interpolation is done as each touching area is encountered. A set of x-coordinates and y-coordinates is generated for each touching area made up of the x and y values of a number of contour points up to and including one of the touching points, the x and y coordinates of the straight line segment connecting the touching points, the x and y values of a number of non-contour points beyond and including the other touching point. The x coordinates and the y coordinates are each fit separately using orthogonal polynomials whose highest degree is specified in the control file, typically 4. The number of points to use along the contour before and after the touching point is specified in the control file, typically 15. The straight line data is weighted. The weight is also specified in the control file and is typically 0.15. The straight line data between the touching points is then replaced with the calculated least squares function. It is found that this procedure generally fills in the appropriate "missing" contour segments. Any standard least squares fitting algorithm may be used, for example those supplied by Numerical Algorithms Group.

In some cases where two filaments "interlock", i.e., touch over large regions, it may not be possible to accurately generate the missing filament contour.

Referring to step 116, a microscope slide may have some dirt or dust particles on it which will also be traced along with the filaments. These are generally much smaller than the filaments. A parameter in the control file specifies an area, in units of square pixels, which is used as an area threshold to discriminate against unwanted small objects. After each object is separated above, its area is calculated and compared with the area threshold. If the area is smaller than the area threshold, its trace is eliminated from the image data.

In step 117, one of the input parameters in the control file is used as a flag to indicate whether the image contains voided filaments.

In step 118, voids are matched with the filaments they are part of in the following way. Previously, all filament contours in the image have been assigned a particular grey level, G1, and all void contours have been assigned a particular grey level, G2, different from that of the filaments. An auxiliary image frame may be used for this purpose. For a given void, all filaments are polled by checking the grey level in the image along straight lines which connect the void center with the centers of each filament. The filament for which the straight line does not pass over any image points at grey level G1 is the filament to which the void belongs. In checking the grey levels along the lines, a 3 pixel by 3 pixel region, centered at each straight line point, is polled. This overcomes potential problems which could result from the fact that the image contours are made up of integer-valued locations. Unmatched voids, e.g., those whose associated filament touches the (reduced) image border, are eliminated from the image data.

This automatic void-filament matching procedure works well for e.g., round, square or triangular, voided filaments, which make up the majority of those analyzed in certain applications. In some cases such as, for example, with more unusual or irregularly shaped voided filaments, the procedure may be implemented with manual matchup.

In step 119, the operator is given the opportunity to manually delete any object which has been traced and outlined on the monitor. This is done by using a keyboard key which moves a selection cursor from center to center of the traced objects. Another key allows selection of the deletion function. Once deleted, the trace of the object is erased and the object is eliminated from the image data.

A noted above in step 102, if a camera/video digitizer combination is used which results in so-called "non-square pixels", the traced x,y data for a filament represents a distorted filament shape. In step 120 in the processing, this distortion is corrected, if necessary, to obtain the true filament shape prior to calculation of filament parameters.

In step 121, the Fourier shape parameters are now calculated. The particular Fourier representation which has been used results from expanding the complex radius vector, from the filament center to the contour points, in terms of the arc length along the filament contour measured from the first traced point on the contour. The properties of such Fourier parameters in general and their method of calculation are well known in the literature although the same have never been applied to the representation of fiber cross sectional shapes in the method of the present invention.

The Fourier shape parameters representing each filament are stored in a data file, one file for each filament. In the case of a filament with voids, the file contains the shape parameters for the outer filament contour followed by a file for the shape parameters for each void. These files are passed to the ray trace program which reads them in and uses the shape parameters to generate the filament shapes. A naming convention is used for automated handling of filaments with and without voids.

Detailed program and related data and information concerning the methods of the present invention are set forth in the Microfiche Appendix referred to above which is incorporated herein by reference.

The method of the present invention provides results which are significantly more accurate for touching images than presently available methods such as practiced with presently available commercial equipment as described above. An important advantage arises from analyzing the image touching points rather than using standard global binary image processing techniques (e.g. erosion, dilation, etc.) which tend to modify shapes of objects in the image. More specifically, the present invention i) uses contour curvature values to automatically locate touching points, ii) provides for automatic matchup of touching point pairs, iii) uses a program algorithm to separate objects after touching point matchup, and iv) provides for a method of interpolating the missing contour data in the touching areas.

For a given yarn sample comprised of a bundle of filaments, all cross sectional shapes of the filaments in the yarn may be determined by the method of this invention and then submitted to the luster prediction method steps for determination of a representative luster for the yarn bundle. These steps can be performed as a part of the yarn manufacturing process and as a quality control function.

The method of the present invention along with its implementing algorithm can be implemented on most computer systems with sufficient memory. Commercially available equipment (the computer, camera, microscope, etc.) can be used in its customary operating manner. The method is not limited, however, to images of microscopic objects but can be used, for example, in a machine vision inspection system for measuring touching discrete parts.

This embodiment of the invention was used in a manufacturing process to select spinneret plates from which fiber filaments are extruded to manufacture yarn used in carpets and to remove from the process those spinneret plates which, because of wear in the manufacturing process or for other reasons as explained below, failed to produce fiber cross sections with luster properties within a desired specification range, all without the need for the intervention of subjective judgment in the manufacturing process.

It is known in the art that the actual cross sectional shape imparted to melt extruded filaments generally conforms to the cross sectional shape of the spinneret plate orifice (see U.S. Pat. No. 3,478,389). But, because of unavoidable variations in spinning conditions, a desired filament cross section may not be achieved. Therefore, certain non-uniformities can be expected in yarns produced from different spinneret plates. This is the case even though the spinneret plate orifices have the same nominal cross sectional shape and size.

Non-uniformities in yarns comprising a carpet arising from variations in cross sectional shape from different threadlines affect the perceived luster. Such non-uniformities give rise to undesirable visual appearance in the carpet referred to as streaking. Accordingly, it is desirable to be able to predict the visual appearance of a yarn, and in particular the luster component of appearance, produced by a given spinneret plate. Thus, if it can be ascertained in advance whether the yarn from a given spinneret plate is compatible with yarn produced produced from other spinneret plates, undesirable carpet streaking can be prevented by controlling the manufacturing process of the yarn at the point of manufacture thereof. This can be accomplished with the method of the present invention by pulling yarn samples, testing these samples according to the method of the invention and then culling out those spinneret plates which do not yield yarns of the appropriate luster uniformity. The invention makes such an approach practical and much less time consuming and expensive than the prior art methods of performing quality assurance tests on commercial quantities of yarn.

In the case referred to above, fiber bundle samples were prepared as described above, individual cross sectional shapes derived and the resulting luster properties determined all in accordance with the method of the present invention. As a result, it was possible to exercise effective manufacturing control of fiber luster in a rapid and inexpensive manner as a part of manufacturing procedures.

The method of separating the individual touching shapes from a bundle or cluster of touching shapes also has applications other than those associated with the cross sectional shapes of touching fibers. It is more generally useful in a wide class of applications with touching particles or objects other than yarn filaments. The same method may be used, for example, to determine individual shape contours of particles in sediments or for shape profile analysis of biological samples.

In addition, once the individual contour shapes have been derived, other parameters such as modification ratio (defined above) of the individual fiber filaments can be determined. The method is thus also useful for deriving such further descriptive parameters of the individual fibers from a group of filaments, some of which are in a touching configuration.

Various other applications will occur to those skilled in the art.

It is to be understood that the disclosure of the embodiments presented herein are set forth in detail for the purpose of making a full and complete disclosure thereof and not by way of limitation. Accordingly, various changes, modifications and substitutions in the embodiments presented will occur to those skilled in the art and the same are to be understood as falling within the scope of the present invention as defined in the appended claims.

What is claimed is:

1. A computer based method of determining the luster properties of filamentary fiber comprising:

a) determining the cross sectional shape of a selected fiber taken along a plane substantially perpendicular to the longitudinal axis of said selected fiber and forming electronic data defining said cross sectional shape;

b) programming and operating a digital computer to derive from said cross sectional shape defining electronic data a mathematical model of the shape of the peripheral contour of said cross sectional shape;

c) simulating by means of electronic processing the impingement of light on said selected fiber by simulating the impingement of light on said mathematical model from a selected direction at an angle of impingement of between 0° and 90° to said longitudinal axis;

d) determining by means of electronic processing from said simulated impingement of light on said mathematical model of said cross sectional shape the distribution pattern of said simulated impinging light after the interaction thereof with said selected fiber; and e) correlating said determined distribution pattern with stored subjective data relating such stored data to luster properties and thereby determining the luster properties of said selected fiber from said cross sectional shape.

2. A method of determining the luster properties of filamentary fiber as set forth in claim 1 wherein said cross sectional shape is determined by exposing the actual cross sectional shape of one or more physical fibers taken along a plane substantially perpendicular to the longitudinal axis thereof and scanning said cross sectional shape thereof.

3. A method of determining the luster properties of filamentary fiber as set forth in claim 2 wherein said cross sectional shape is determined by exposing the actual cross sectional shapes of a plurality of touching fibers in a group and scanning and deriving therefrom information defining the cross sectional shapes of the individual fibers in the group.

4. A method of determining the luster properties of filamentary fiber as set forth in claim 1 including the steps of simulating the rotational indexing of said representative fiber about said longitudinal axis through a plurality of fixed positions, simulating said impingement of light in each of said fixed positions, and determining said distribution pattern at each of said fixed positions.

5. A method of determining the luster properties of filamentary fiber as set forth in claim 4 wherein the rotational intervals between said fixed positions are less than about 10°.

6. A method of determining the luster properties of filamentary fiber as set forth in claim 5 wherein said rotational intervals are less than about 5°.

7. A method of determining the luster properties of filamentary fiber as set forth in claim 6 wherein said rotational intervals are less than about 3°.

8. A method of determining the luster properties of filamentary fiber as set forth in claim 1 wherein said mathematical model of said peripheral contour of said cross sectional shape is expressed in the form of Fourier transform functions.

9. A method of determining the luster properties of filamentary fiber as set forth in claim 8 wherein said cross sectional shape is determined by exposing the actual cross sectional shape of one or more physical fibers taken along a plane substantially perpendicular to the longitudinal axis thereof and scanning said cross sectional shape thereof.

10. A method of determining the luster properties of filamentary fiber as set forth in claim 9 wherein said cross sectional shape is determined by exposing the actual cross sectional shapes of a plurality of touching fibers in a group and scanning and deriving therefrom information defining the cross sectional shapes of the individual fibers in the group.

11. A method of determining the luster properties of filamentary fiber as set forth in claim 8 including the steps of simulating the rotational indexing of said representative fiber about said longitudinal axis through a plurality of fixed positions, simulating said impingement of light in each of said fixed positions, and determining said distribution pattern at each of said fixed positions 12. A method of determining the luster properties of filamentary fiber as set forth in claim 11 wherein the rotational intervals between said fixed positions are less than about 10°.

13. A method of determining the luster properties of filamentary fiber as set forth in claim 11 wherein said rotational intervals are less than about 5°.

14. A method of determining the luster properties of filamentary fiber as set forth in claim 11 wherein said rotational intervals are less than about 3°.

15. A method of determining the luster properties of filamentary fiber as set forth in claim 4 wherein said simulated impingement of light is in the form of a selected statistically significant number of discrete photons, the paths of each of said photons upon interaction with said mathematical model of said fiber cross sectional shape are traced, and the cumulative effect of such interaction of said discrete photons is determined to thereby determine said distribution pattern.

16. A method of determining the luster properties of filamentary fiber as set forth in claim 15 wherein the rotational intervals between said fixed positions are less than about 10°.

17. A method of determining the luster properties of filamentary fiber as set forth in claim 15 wherein the rotational intervals between said fixed positions are less than about 5°.

18. A method of determining the luster properties of filamentary fiber as set forth in claim 15 wherein the rotational intervals between said fixed positions are less than about 3°.

19. A method of determining the luster properties of filamentary as set forth in claim 16, 17 or 18 wherein said mathematical model of said peripheral contour of said cross sectional shape is expressed in the form of Fourier transform functions.

20. A method of determining the luster properties of filamentary fiber as set forth in claim 1 wherein said simulated impingement of light is in the form of a selected statistically significant number of discrete photons, the paths of each of said photons upon interaction with said mathematical model of said fiber cross sectional shape are traced, and the cumulative effect of such interaction of said discrete photons is determined to thereby determine said distribution pattern.

21. A method of controlling the luster properties of filamentary fiber in a manufacturing process comprising:

a) preparing a sample of one or more filaments of a fiber as manufactured in a manufacturing process which is to be controlled;

b) determining the cross sectional shape of at least one selected filament of said fiber filaments along a plane substantially perpendicular to the longitudinal axis thereof;

c) deriving a mathematical model of the shape of the peripheral contour of said cross sectional shapes;

d) simulating the impingement of light on said selected fiber filament from a selected direction at an angle of impingement of between 0° and 90° to said longitudinal axis;

e) determining from a mathematical representation of said simulated impinging light and said mathematical model of said cross sectional shape the distribution pattern of said simulated impinging light after the interaction thereof with said selected fiber filament;

f) correlating said determined distribution pattern with subjective data relating such data to luster properties and thereby determining the luster properties of said selected fiber from said cross sectional shape; and g) adjusting selected manufacturing parameters of said manufacturing process to control luster properties of the fiber being manufactured based on the luster properties so determined.

22. A method of controlling the luster properties of filamentary fiber in a manufacturing process as set forth in claim 21 wherein said cross sectional shape is determined by exposing the actual cross sectional shape of one or more physical fibers taken along a plane substantially perpendicular to the longitudinal axis thereof and scanning said cross sectional shape thereof.

23. A method of controlling the luster properties of filamentary fiber in manufacturing process as set forth in claim 22 wherein said cross sectional shape is determined by exposing the actual cross sectional shapes of a plurality of touching fibers in a group and scanning and deriving therefrom information defining the cross sectional shapes of the individual fibers in the group.

24. A computer based method of determining the individual contour shapes of a plurality of objects in a group and generating electronic data representative of said contour shapes, at least some of which objects are in a touching relationship to each other comprising:

a) preparing a planar representation of an image of the contours of the group of objects whose individual contours are to be determined and forming electronic data defining said image;

b) electronically processing said electronic image defining data to determine for each of a selected group of said objects as represented in said image the curvature rates of the peripheral paths of the contour shapes thereof as a function of the linear dimensions thereof;

c) identifying by means of electronic processing regions of said peripheral paths in which said curvature rates of said contour shapes exceed a preselected threshold level;

d) identifying by means of electronic processing the regions in which said threshold level is exceeded as touching point candidates representing regions of possible touching contact between said contour shapes;

e) matching by means of electronic processing said touching point regions into matched touching point pairs and discarding from the data those matching point candidates which do not form matched pairs;

f) separating by means of electronic processing said contour shapes in the regions of said matched touching point pairs; and g) interpolating by means of electronic processing said contour shapes over the separated regions of said touching points in which said contour shapes are missing by reason of said separation by utilizing mathematical functions representative of said contour shapes immediately adjacent said missing contour shape regions to thereby reconstruct the missing contour shapes in said touching point regions and complete the extraction of said individual contour shapes to derive electronic data representative of the individual contour shapes of said objects.

25. A method of determining the individual contour shapes of a plurality of objects in a group, at least some of which objects are in a touching relationship to each other as set forth in claim 18 including the additional step of determining from said individual contour shapes the modification ratio of the individual fiber filaments.

* * * * *

UNITED STATES PATENT AND TRADEMARK OFFICE
CERTIFICATE OF CORRECTION

PATENT NO. : 5,299,133
DATED : March 29, 1994
INVENTOR(S) : Henry Kobsa et al.

It is certified that error appears in the above-indentified patent and that said Letters Patent is hereby corrected as shown below:

Col. 10, line 28, Equation 19, "$\Gamma = \sqrt{[n'^2 - n^2 + (\{s\}\text{dot prod.}\{o\})^2]}\{s\}\text{dot prod.}\{o\}$" should be -- $\Gamma = \sqrt{[n'^2 - n^2 + (\{s\}\text{dot prod.}\{o\})^2]} - \{s\}\text{dot prod.}\{o\}$ --; Col. 16, lines 46-47, there should be no paragraph break. Line 47 should be moved up to connect with line 46; Col. 16, lines 51-52, there should be no paragraph break. Line 52 should be moved up to connect with line 51; Col. 28, line 42, "18" should be -- 24 --.

Signed and Sealed this

Fourth Day of October, 1994

Attest:

BRUCE LEHMAN

*Attesting Officer*   *Commissioner of Patents and Trademarks*